US012776403B2

(12) United States Patent
Park et al.

(10) Patent No.: US 12,776,403 B2
(45) Date of Patent: Oct. 27, 2026

(54) METHOD OF DETERMINING CONTINUOUS DRUG DOSE USING REINFORCEMENT LEARNING AND PHARMACOKINETIC-PHARMACODYNAMIC MODELS

(71) Applicant: POSTECH Research and Business Development Foundation, Pohang-si (KR)

(72) Inventors: Sung Min Park, Pohang-si (KR); Seung Hyun Lee, Daegu (KR)

(73) Assignee: POSTECH RESEARCH AND BUSINESS DEVELOPMENT FOUNDATION, Pohang-si (KR)

( * ) Notice: Subject to any disclaimer, the term of this patent is extended or adjusted under 35 U.S.C. 154(b) by 1211 days.

(21) Appl. No.: 17/535,474

(22) Filed: Nov. 24, 2021

(65) Prior Publication Data

US 2022/0199217 A1 Jun. 23, 2022

(30) Foreign Application Priority Data

Dec. 18, 2020 (KR) .......................... 10-2020-178132

(51) Int. Cl.
*G16H 20/17* (2018.01)
*G16B 40/00* (2019.01)
(Continued)

(52) U.S. Cl.
CPC ............. *G16H 20/17* (2018.01); *G16B 40/00* (2019.02); *G16H 50/20* (2018.01); *G16H 70/40* (2018.01)

(58) Field of Classification Search
CPC .... G01N 2800/52; G16H 50/20; G16H 20/10; G16H 50/70; G16H 50/50; G16H 70/40;
(Continued)

(56) References Cited

U.S. PATENT DOCUMENTS

2012/0246106 A1* 9/2012 Atlas ...................... G16H 50/20 700/282
2019/0214124 A1* 7/2019 Mougiakakou ........ G16H 20/17
(Continued)

FOREIGN PATENT DOCUMENTS

KR 1020160022874 A 3/2016
KR 1020200063960 A 6/2020
(Continued)

OTHER PUBLICATIONS

Schamberg, G. et al. Controlling level of unconsciousness by titrating propofol with deep reinforcement learning. AIME 2020, LNAI 12299, pp. 26-36, 2020. (Year: 2020).*
(Continued)

*Primary Examiner* — Mary K Zeman
(74) *Attorney, Agent, or Firm* — Morgan, Lewis & Bockius LLP

(57) ABSTRACT

A method of determining a continuous drug dose using reinforcement learning and a pharmacokinetic-pharmacodynamic model according to an embodiment of the present invention includes, measuring or estimating a patient's pharmacokinetic-pharmacodynamic model; training a reinforcement learning algorithm using drug infusion data and patient state data based on the pharmacokinetic-pharmacodynamic model; and automatically determining a continuous drug dose by the trained reinforcement learning algorithm.

20 Claims, 5 Drawing Sheets

(51) Int. Cl.
*G16H 50/20* (2018.01)
*G16H 70/40* (2018.01)

(58) Field of Classification Search
CPC .... G16H 10/60; C12Q 2600/106; G16B 5/00; G16B 40/00; G16B 40/20; G06N 20/00; G06N 3/092
See application file for complete search history.

(56) References Cited

U.S. PATENT DOCUMENTS

| | | | | |
|---|---|---|---|---|
| 2020/0337648 | A1* | 10/2020 | Saripalli | G06N 20/00 |
| 2022/0189603 | A1* | 6/2022 | Damiano | G06F 21/34 |
| 2022/0199217 | A1* | 6/2022 | Park | G16B 40/00 |

FOREIGN PATENT DOCUMENTS

| | | | | |
|---|---|---|---|---|
| KR | 1020110119409 A | | 11/2022 | |
| WO | WO-2015067856 A1 | * | 5/2015 | B32B 29/002 |
| WO | WO-2015067956 A1 | * | 5/2015 | A61M 5/1723 |

OTHER PUBLICATIONS

Gaweda, A. E. et al. Individualization of pharmacological anemia management using reinforcement learning. Neural Networks, vol. 18, p. 826-834, 2006. (Year: 2006).*

Gaweda, A. E. et al. Incorporating prior knowledge into Q-learning for drug delivery individualization. ICMLA '05, 2005, 6 pages, hereinafter, Gaweda 2. (Year: 2005).*

Lee, S. et al. Toward a fully automated artificial pancreas system using a bioinspired reinforcement learning design. IEEE Journal of Biomedical and Health Informatics vol. 25, No. 2 p. 536-546 (Feb. 2021). (Year: 2021).*

Ribba et al. model-informed artificial intelligence: reinforcement learning for precision dosing. Apr. 2020, Clinical Pharmacology & therapeutics. vol. 107, No. 4, p. 853-858. (Year: 2020).*

Yu, Y. et al. PK/PD approaches. Chapter 57 in Drug Discovery and Evlauation: Methods in Clinical Pharmacology, p. 1047-1069, 2020. (Year: 2020).*

Chambers, D. J. (2018) Principles of intravenous drug infusion. Pharmacology, Anesthesia and Intensive Care Medicine, vol. 20 No. 1, p. 61-65. (Year: 2018).*

Yu, C. et al. Reinforcement learning in healthcare: a survey. ACM computing surveys, vol. 55, No. 1, article 5, Nov. 2021, 36 pages. (Year: 2021).*

Lee et al. Toward a Fully Automated Artificial Pancreas System Using a Bioinspired Reinforcement Learning Design: In Silico Validation. IEEE J of Biomed and Health Informatics, vol. 25, No. 2, p. 536-546. Earliest date of publication: Jun. 12, 2020. (Year: 2020).*

Javad, M. et al. (2015) Reinforcement learning algorithm for blood glucose control in diabetic patients. Proceedings of the ASME 2015 International Mechanical Engineering Congress and Exposition IMECE2015, Nov. 13-19, 2015, Houston, Texas. 9 pages. (Year: 2015).*

Korean Office Action in KR 10-2020-0178132, dated Apr. 28, 2022, 10 pages including translation.

* cited by examiner

METHOD OF DETERMINING CONTINUOUS DRUG DOSE USING REINFORCEMENT LEARNING AND PHARMACOKINETIC-PHARMACODYNAMIC MODELS

BACKGROUND OF THE INVENTION

1. Field of the Invention

The present application relates to a method of determining continuous drug dose using reinforcement learning and pharmacokinetic-pharmacodynamic models.

2. Description of the Related Art

Continuous drug administration using a drug infusion pump is a management and treatment method used in various medical fields such as cancer, diabetes, pain management, and anesthesia, where it is necessary to control a patient's state for a long period of time.

In general, the infusion amount of the drug infusion pump is monitored by the medical staff at all times, and it is directly input according to the patient's state or a predetermined time-specific infusion amount profile is used without modification.

Recently, as an alternative to a shortage of medical personnel or for efficiency, the application of closed-loop algorithms for automated infusion amount determination and infusion to drug infusion pumps has been widely studied.

There is a problem that pharmacological properties of a drug are different for each patient and vary greatly depending on the patient's state. This problem can be solved to some extent by artificial intelligence learning algorithm such as reinforcement learning.

However, the problem of time delay of effect of the infused drug makes it difficult for the algorithm to respond to a sudden change in the patient's state, and there is always a risk of drug overinfusion of the drug infusion automation algorithm.

SUMMARY OF THE INVENTION

Problem to be Solved by the Invention

Therefore, there is a need in the art for implementing a learning algorithm that considers drug effect delay while continuously infusing a drug through an automated drug infusion pump.

Means for Solving the Problem

In order to solve the above problem, an embodiment of the present invention provides a method for determining a continuous drug dose using reinforcement learning and a pharmacokinetic-pharmacodynamic model.

The method of determining a continuous drug dose using reinforcement learning and a pharmacokinetic-pharmacodynamic model includes: measuring or estimating a patient's pharmacokinetic-pharmacodynamic model; training a reinforcement learning algorithm using drug infusion data and patient state data based on the pharmacokinetic-pharmacodynamic model; and automatically determining a continuous drug dose by the trained reinforcement learning algorithm.

Further, the means for solving the above problem do not enumerate all the features of the present invention. Various features of the present invention and its advantages and effects may be understood in detail with reference to the following specific embodiments.

According to an embodiment of the present invention, it is possible to learn a continuous drug infusion algorithm of an individual patient, and the automated drug infusion algorithm can be continuously updated without the risk of overdose.

DETAILED DESCRIPTION OF THE PREFERRED EMBODIMENT

Figure 1:
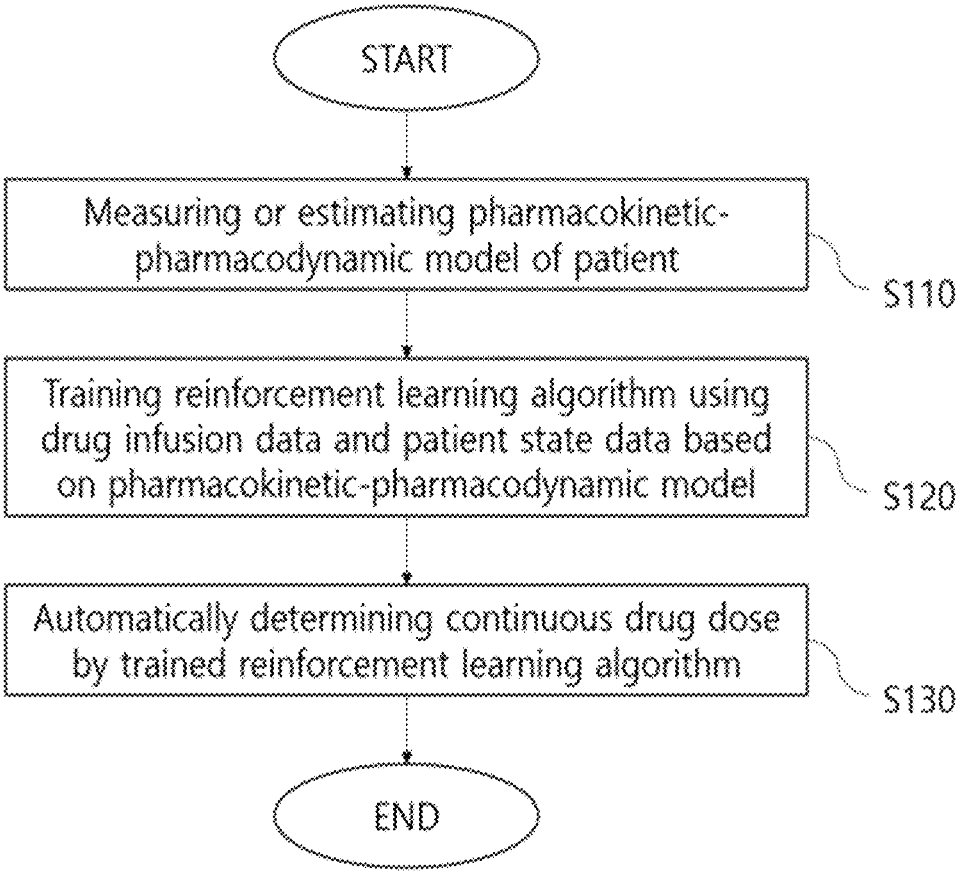
FIG. 1 is a flowchart of a method for determining a continuous drug dose using reinforcement learning and a pharmacokinetic-pharmacodynamic model according to an embodiment of the present invention.

Hereinafter, preferred embodiments will be described in detail so that those of skilled in the art can easily practice the present invention with reference to the accompanying drawings. In the detailed description of the preferred embodiments of the present invention, if it is determined that a specific description of a related well-known function or feature may unnecessarily obscure the gist of the present invention, the specific description thereof will be omitted. In addition, the same reference numerals are used throughout the drawings for features having similar functions and operations.

Further, throughout the specification, when a part is said to be 'connected' with another part, it includes not only the case where they are 'directly connected' but also the case where they are 'indirectly connected' with another element interposed therebetween. Furthermore, 'including' a feature means that other features may be further included, rather than excluding other features, unless otherwise stated.

FIG. 1 is a flowchart of a method of determining a continuous drug dose using reinforcement learning and a pharmacokinetic-pharmacodynamic model according to an embodiment of the present invention.

Referring to FIG. 1, the method of determining a continuous drug dose using reinforcement learning and a pharmacokinetic-pharmacodynamic model according to an embodiment of the present invention includes, measuring or estimating a patient's pharmacokinetic-pharmacodynamic model (S110), training a reinforcement learning algorithm using drug infusion data and patient state data based on the pharmacokinetic-pharmacodynamic model (S120), and automatically determining a continuous drug dose by the trained reinforcement learning algorithm (S130).

Here, the reinforcement learning algorithm may use Pharmacokinetic/Pharmacodynamic (PK/PD) characteristics, which mean drug effects in pharmacology, as a discount rate corresponding to conversion of a reward to the present value. In addition, since measuring or estimating the pharmacokinetic-pharmacodynamic model may be performed according to technologies known to those skilled in the art, detailed descriptions thereof will be omitted.

In addition, the drug effects may be divided into short-term effects and long-term effects. In this case, the short-term effects may use a PK/PD curve as it is as the discount rate, and the long-term effects (i.e. cumulative effects) may use the integral value of the PK/PD curve as the discount rate.

The method of determining the continuous drug dose using reinforcement learning and the pharmacokinetic-pharmacodynamic model described above with reference to FIG. 1 may be performed by a processing device capable of executing a reinforcement learning algorithm.

Hereinafter, with reference to FIGS. 2 to 4, a method of determining a continuous drug dose using reinforcement learning and the pharmacokinetic-pharmacodynamic model according to embodiments of the present invention will be described in detail.

Figure 2:
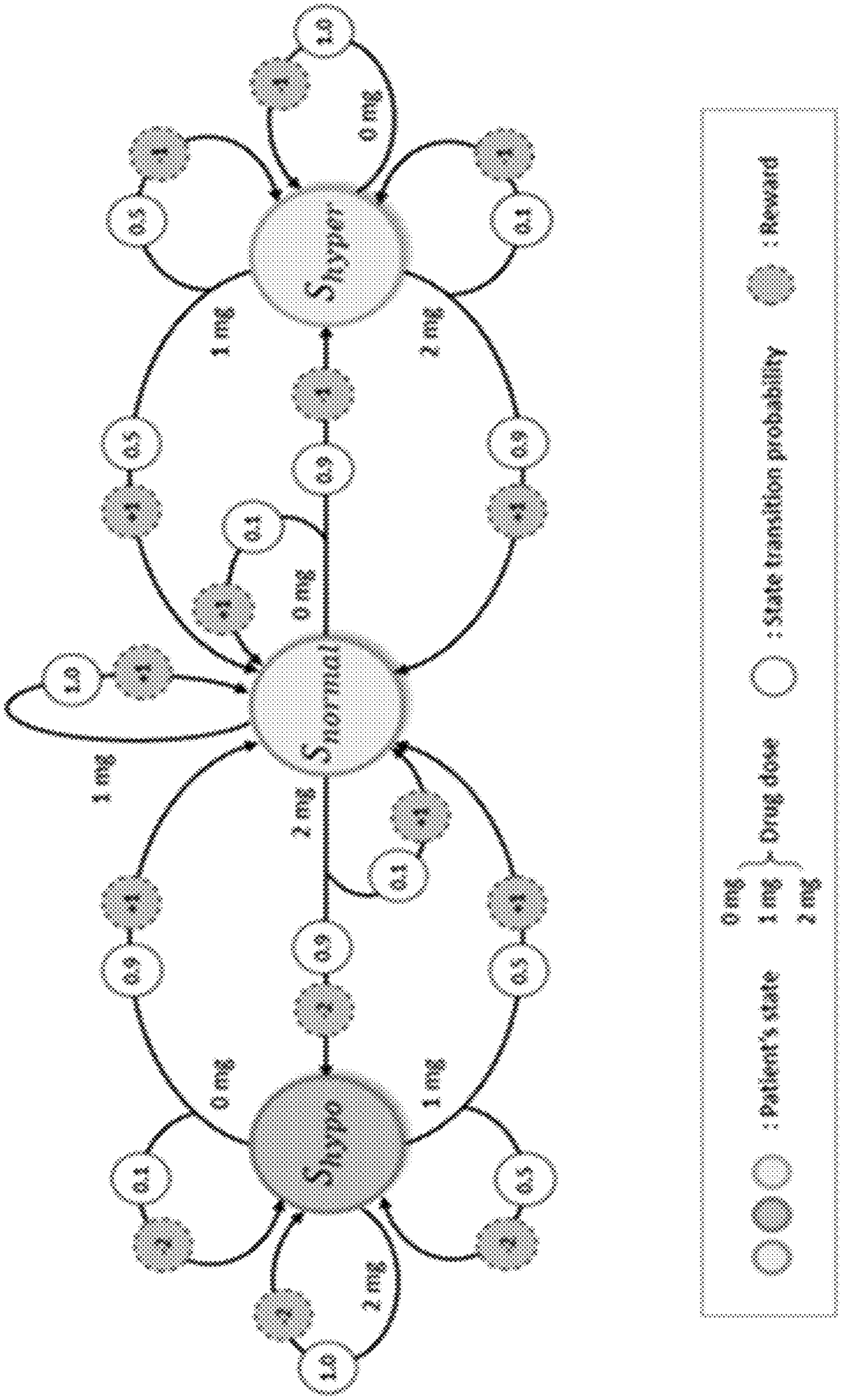
FIG. 2 is a diagram showing a problem definition model for applying a reinforcement learning algorithm to determination of a continuous drug dose according to an embodiment of the present invention.

FIG. 2 is a diagram showing a problem definition model for applying the reinforcement learning algorithm to determination of the continuous drug dose according to an embodiment of the present invention.

Referring to FIG. 2, in the reinforcement learning algorithm, the patient's state may include a normal state ($S_{normal}$), an underinfusion state ($S_{hyper}$), and an overinfusion state ($S_{hypo}$). Here, the normal state ($S_{normal}$) means a state in which an appropriate amount of a drug is infused, the underinfusion state ($S_{hyper}$) means a state caused by underinfusion of the drug, and the overinfusion state ($S_{hypo}$) means a state caused by overinfusion of the drug.

Further, when selectable drug doses are 0 mg, 1 mg, and 2 mg, an example of the problem definition model for applying the reinforcement learning algorithm to continuous drug dose determination is shown in FIG. 2. Here, reinforcement learning is an artificial intelligence algorithm that learns a decision that maximizes long-term expected rewards, and is suitable for optimizing successive decisions.

Even if the same amount of drug is administered, the same drug effect does not always appear, so the patient's state changes according to a state transition probability. When the state changes, different rewards may be given according to the changed state.

For example, in the case that the drug of 2 mg is selected at the normal state ($S_{normal}$), there is a 90% probability of transition to the overinfusion state ($S_{hypo}$) and receiving the reward of −2.

On the other hand, in the case that 0 mg is selected at the normal state ($S_{normal}$), there is a 90% probability of transition to the underinusion state ($S_{hyper}$) and receiving the reward of −1.

However, in the case that the drug of 1 mg is selected at the normal state ($S_{normal}$), the normal state ($S_{normal}$) can be maintained with a 100% probability, and in this case, the reward of 1 is received.

As above, if only the patient's treatment record and reward criteria according to the state are given, the reinforcement learning algorithm can learn through repeated updates that 1 mg, 0 mg, and 2 mg should be infused at the normal state ($S_{normal}$), the overinfused state ($S_{hypo}$), and the underinfused state ($S_{hyper}$), respectively.

This principle can be equally applied to much more complex actual patient conditions, types of drugs, dosages of drugs, and reactions to drugs.

However, there is a limit in that it is difficult to respond to the drug effect delay using this principle alone.

Pharmacokinetics is the study of the absorption, distribution, metabolism, and excretion of drugs. Pharmacodynamics is essentially the study of the physiological and biochemical actions of drugs on the body and their mechanisms, i.e. the responses of the body caused by the drugs. In other words, pharmacokinetics corresponds to changes in blood concentration of an infused drug over time, and pharmacodynamics corresponds to changes in drug effects according to blood drug concentrations. Together, the drug effects and changes over time are referred to as the pharmacokinetic-pharmacodynamic (PK-PD) model.

On the other hand, a general reinforcement learning algorithm is evaluated and updated in consideration of what kind of rewards have been received in the future after a current action, and how these rewards are affected by the current action.

However, in a continuous action decision model, the effectiveness of the current action generally diminishes over time and is diluted by external factors other than the action.

Therefore, with respect to future rewards received after the action decision, the reward received later is considered to be discounted more and this is achieved by multiplying the reward by the discount rate r between 0 and 1. In other words, the reward R received after n steps from the action is applied to the update of the algorithm as $r^n \times R$ discounted by $r^n$.

The present invention intends to apply such a concept of discount of the rewards according to the action with respect to time in combination with pharmacokinetic-pharmacodynamics, which is the concept of changes in effects over time of the infused drug.

Figure 3:
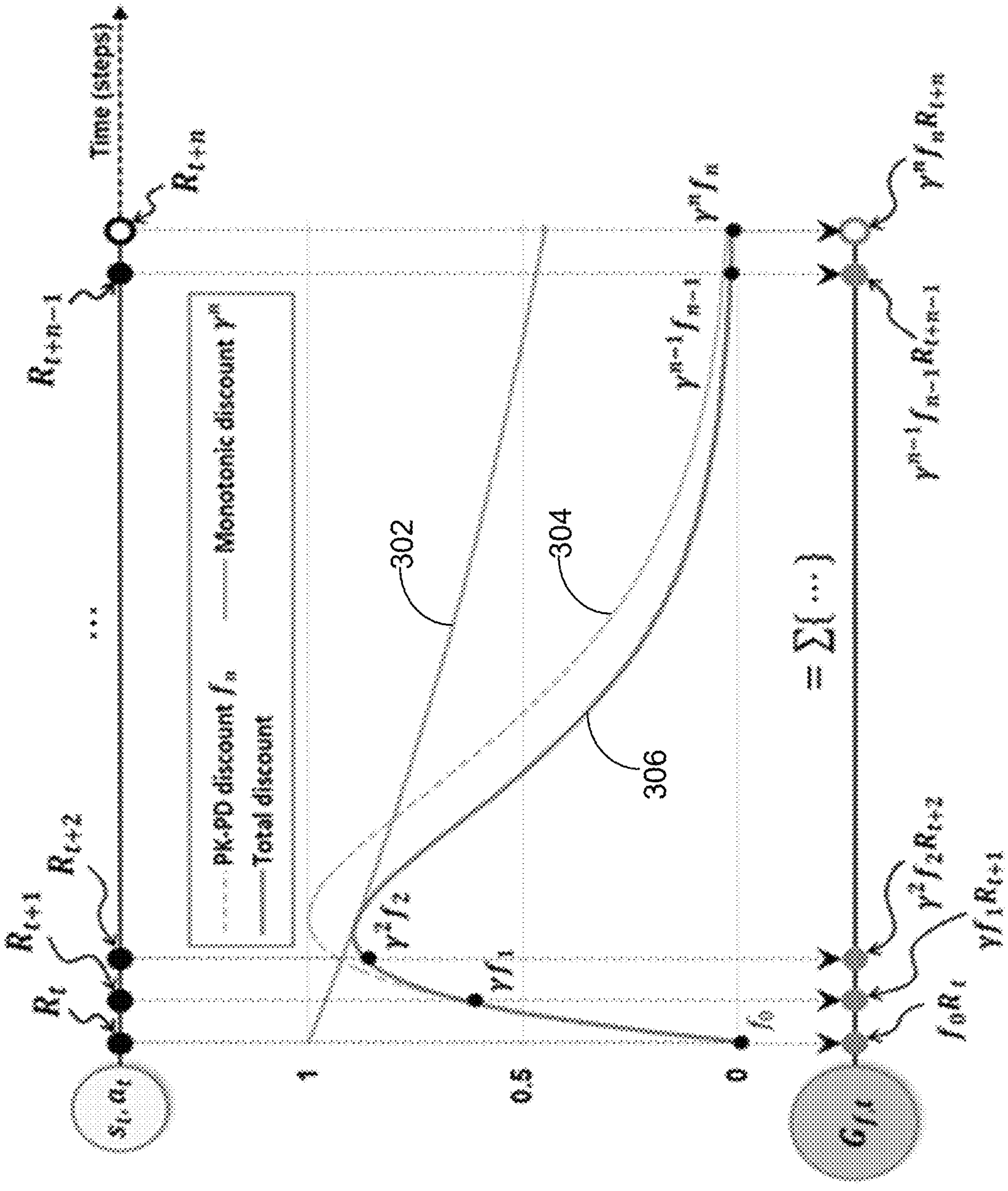
FIG. 3 is a diagram for explaining a discount rate of a reinforcement learning algorithm in the case that a pharmacokinetic-pharmacodynamic model is used according to an embodiment of the present invention.

FIG. 3 shows a diagram for explaining a discount rate of a reinforcement learning algorithm in the case that the pharmacokinetic-pharmacodynamic model is used according to an embodiment of the present invention.

Referring to FIG. 3, in the case that the algorithm selects at as the drug dose at the patient's state st at time t, the patient's state subsequently changes with time by the administered drug, and the rewards $R_t$, $R_{t+1}$, . . . , $R_{t+n}$ are given accordingly.

To evaluate adequacy of the dose at as a process of learning an appropriate drug dose, these rewards are discounted by the time t, taking into account an influence of the action.

The solid line 302 indicates the dilution of the action influence over time by external factors, and represents a monotonic discount rate r", which is generally used in reinforcement learning.

In addition, the dotted line 304 shows the pharmacokinetic-pharmacodynamic model $f_n$, which generally rises after drug infusion and then decreases after the peak.

Finally, the solid line 306 is a combined discount rate for continuous drug administration suggested by the present invention, which can be expressed as $r^n f_n$ by multiplying the monotonic discount rate $r^n$ and the pharmacokinetic-pharmacodynamic model $f_n$.

Therefore, evaluation of the drug dose $a_t$ in the state $s_t$ and algorithm update can be performed by $G_{f,t}$ obtained by multiplying each of the future rewards $R_t$, $R_{t+1}$, . . . , $R_{t+n}$ over time by the combined discount rate and then adding them all together.

On the other hand, the above-mentioned concept can be applied to evaluate cumulative effects, as well as to evaluate the effect of a single time point over time.

Figure 4:
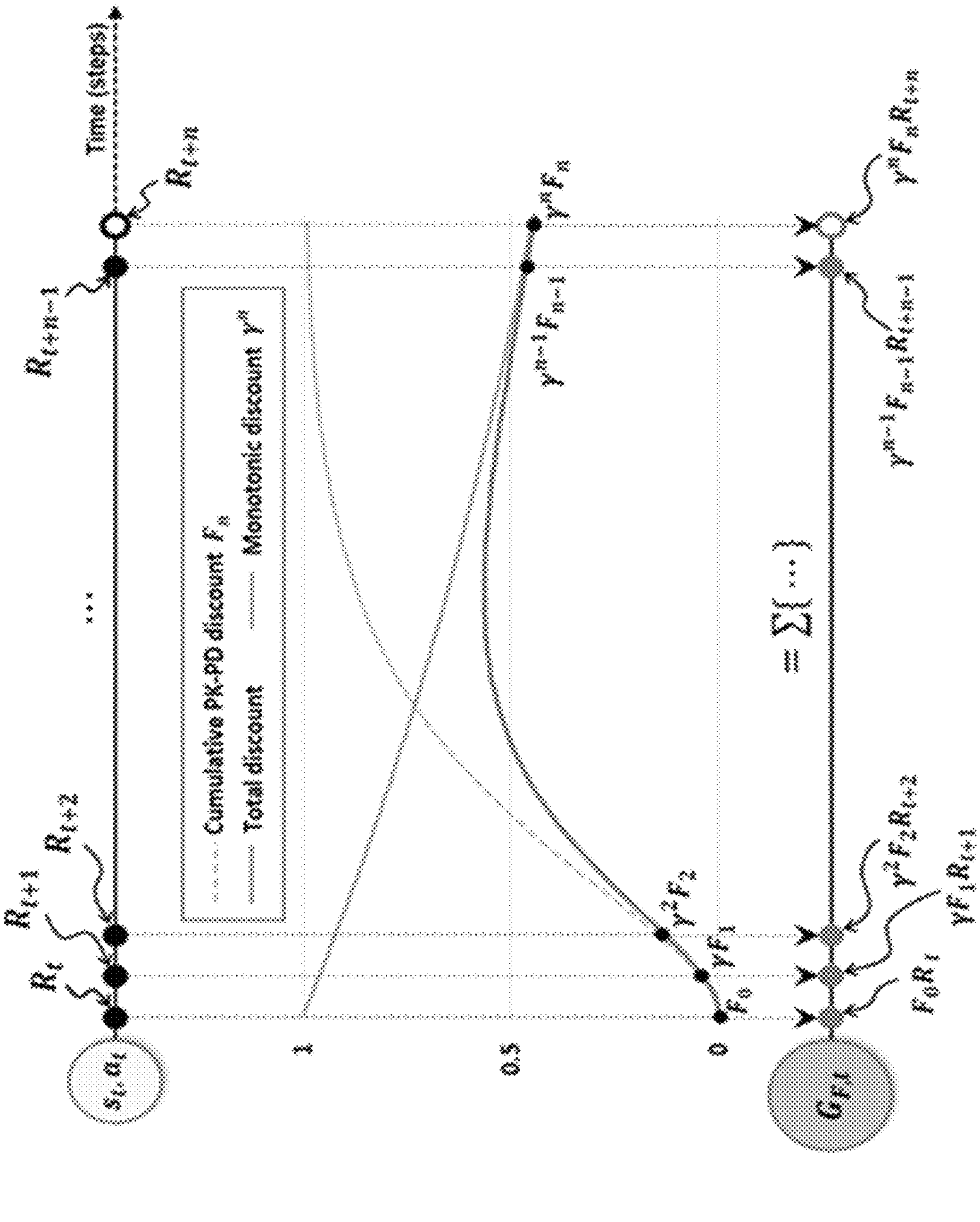
FIG. 4 is a diagram for explaining a discount rate of a reinforcement learning algorithm in the case that a cumulative pharmacokinetic-pharmacodynamic model is used according to an embodiment of the present invention.

FIG. 4 is a diagram for explaining a discount rate of a reinforcement learning algorithm in the case that a cumulative pharmacokinetic-pharmacodynamic model (cumulative PK-PD model) is used according to an embodiment of the present invention. In the same manner as shown in FIG. 3, a combined discount rate calculated using the cumulative PK-PD model shown in FIG. 4 can be used.

Figure 5:
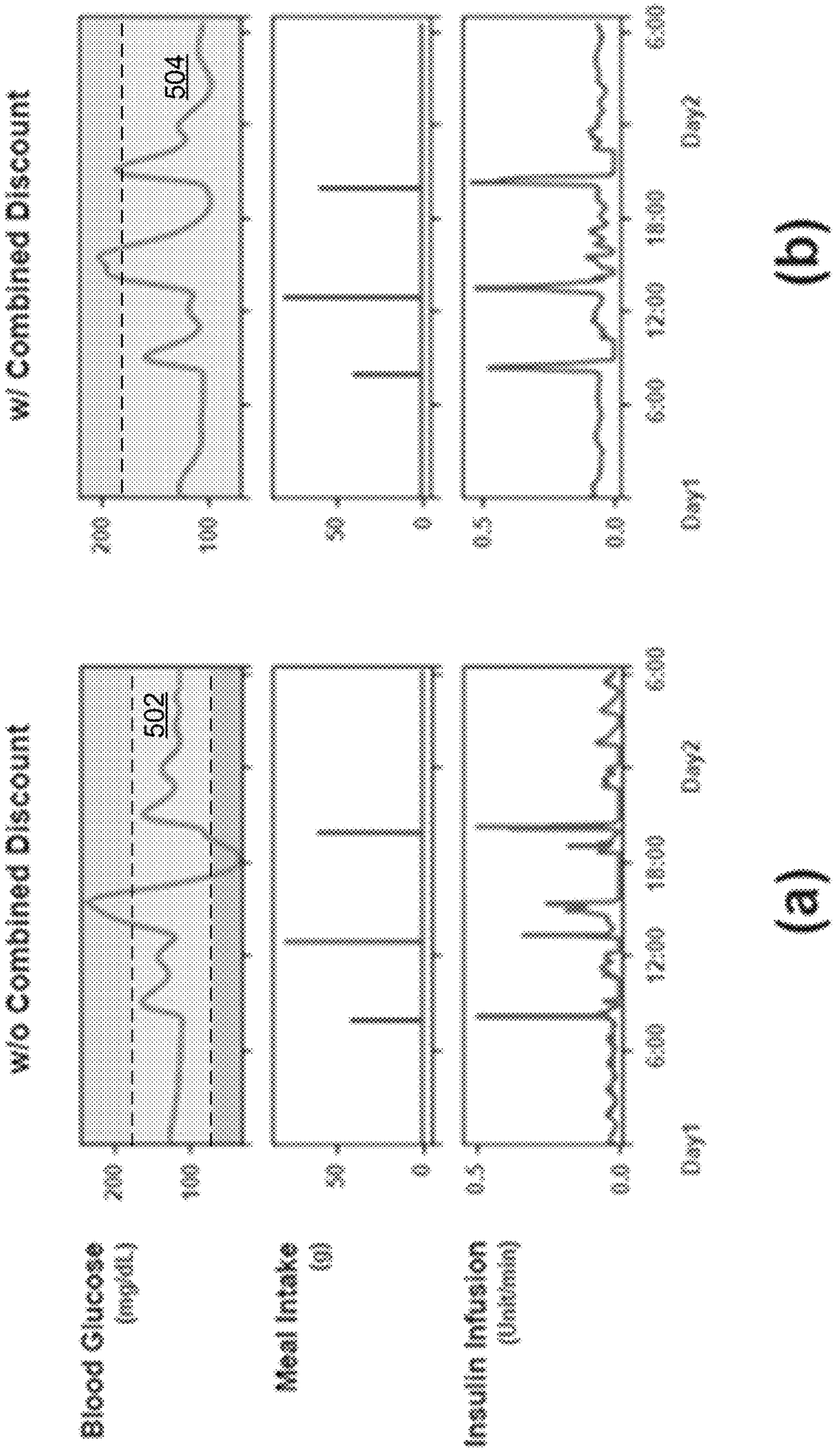
FIGS. 5(*a*) and 5(*b*) are diagrams comparing effects before and after applying a continuous drug dose determination method using reinforcement learning and a pharmacokinetic-pharmacodynamic model according to an embodiment of the present invention.

FIGS. 5(*a*) and 5(*b*) are diagrams comparing the effects before and after applying the continuous drug dose determination method using reinforcement learning and the pharmacokinetic-pharmacodynamic model according to an embodiment of the present invention, and shows results of training the algorithm for determining a continuous insulin infusion rate using reinforcement learning in a virtual diabetic patient simulator approved by the US FDA to replace animal experiments.

In addition, FIG. 5(*a*) shows the results before applying the combined discount rate according to the present invention, and FIG. 5(*b*) shows the results after applying the combined discount rate according to the present invention. The three graphs shown in each of (a) and (b) represent the patient's blood glucose value over time, meals, the amount of insulin infused with a drug infusion pump in order from the top.

Referring to FIGS. 5(*a*) and 5(*b*), the reinforcement learning algorithm determines the insulin infusion rate based on the patient's blood glucose value and infuses the insulin with the drug infusion pump.

Further, in order to evaluate whether or not the continuous drug dose determination method according to the embodiment of the present invention enables automated drug administration without the risk of overinfusion, three meals in the morning/lunch/evening were given to the virtual patient and the amounts of food were not input to the algorithm.

Comparing FIGS. 5(*a*) and 5(*b*), in the case that blood sugar rapidly rose due to excessive eating at lunch, the insulin was over-infused and the virtual patient fell into hypoglycemia between 17:00 and 19:00 (the bottom red area in the top graph) before applying the combined discount rate. On the other hand, after applying the combined discount rate, the insulin was quickly infused after lunch, but the dosage was reduced again after infusing only an appropriate amount as needed, so hypoglycemia did not occur and blood glucose level was well maintained in the normal range (the area 502 or 504 in the top graph).

The continuous drug dose determination method using reinforcement learning and the pharmacokinetic-pharmacodynamic model according to the embodiment of the present invention as described above can be utilized for personalized drug administration of a drug infusion pump as a part of precision medicine.

In addition, since it is possible to automate drug administration without the risk of overdose in consideration of drug effect delay, it can also be utilized in telemedicine for disease management of chronic disease patients.

As a representative example, it can be used in medical fields such as cancer, diabetes, pain management, and anesthesia, and in particular, in the case of diabetes, it can be applied to implement a fully autonomous artificial pancreas that does not require input of a meal amount.

The present invention is not limited by the above embodiments and the accompanying drawings. For those skilled in the art to which the present invention pertains, it will be apparent that the elements according to the present invention can be substituted, modified, and changed without departing from the technical spirit of the present invention.

What is claimed is:

1. A method for administrating drug using reinforcement learning and a pharmacokinetic-pharmacodynamic model, comprising:

determining a diabetic patient's pharmacokinetic-pharmacodynamic model;

training a reinforcement learning algorithm for the diabetic patient using insulin infusion data and patient state data based on the pharmacokinetic-pharmacodynamic model, including:

identifying a plurality of selectable insulin doses including at least two predefined non-zero insulin doses;

obtaining the diabetic patient's treatment record including the insulin infusion data and the patient state data associated with a plurality of infusion events, wherein each infusion event corresponds to a respective one of the plurality of selectable insulin doses, a prior patient state, and a post patient state;

obtaining one or more reward criteria corresponding to a plurality of patient states including an underinfusion state, an overinfusion state, and a normal state;

based on the diabetic patient's treatment record, determining a plurality of transition probabilities for a plurality of state transitions among the plurality of patient states, each transition probability indicating a probability of a respective state change when a respective insulin dose is applied, wherein each respective patient state corresponds to a plurality of groups of transition probabilities for state transitions starting from the respective patient state, and each group of transition probabilities corresponds to a distinct predefined non-zero insulin dose and a total transition probability that is equal to 1;

determining a respective reward score for each of the plurality of state transitions based on the one or more reward criteria;

applying a discount rate to the respective reward score associated with each of the plurality of state transitions based on the diabetic patient's pharmacokinetic-pharmacodynamic model; and determining the reinforcement learning algorithm based on a long-term expected reward;

while infusing insulin to the diabetic patient by an insulin infusion pump, automatically determining a continuous insulin infusion rate by the trained reinforcement learning algorithm, including:

determining a current insulin dose and a current patient state;

applying the trained reinforcement learning algorithm to determine one or more subsequent insulin doses based on the current insulin dose and the current patient state, including:

determining a first reward for a first transition to a distinct patient state based on a first reward criterion of the one or more reward criteria of the diabetic patient;

determining a time-dependent discount rate corresponding to the first transition for the first reward; and adjusting the first reward associated with the first transition based on the time-dependent discount rate; and continuously controlling the insulin infusion pump to infuse the insulin to the diabetic patient based on the continuous insulin infusion rate that is determined based on the trained reinforcement learning algorithm, such that a blood glucose level of the diabetic patient is maintained in a normal range to protect the diabetic patient from hypoglycemia.

2. The method according to claim 1, wherein the reinforcement learning algorithm corresponds to a plurality of pharmacokinetic-pharmacodynamic characteristics associated with the pharmacokinetic-pharmacodynamic model.

3. The method according to claim 1, wherein the trained reinforcement learning algorithm divides drug effects in the pharmacokinetic-pharmacodynamic model into short-term drug effects and cumulative drug effects, and wherein the short-term drug effects use the pharmacokinetic-pharmacodynamic model as the discount rate, and the cumulative drug effects use an integral value of the pharmacokinetic-pharmacodynamic model as the discount rate.

4. The method according to claim 1, wherein the discount rate is a combined discount rate $r^n f_n$ obtained by multiplying a monotonic discount rate $r^n$ and the pharmacokinetic-pharmacodynamic model $f_n$.

5. The method according to claim 1, wherein the reinforcement learning algorithm selects $a_t$ as a target drug dose at the patient state $s_t$ at time t, and rewards $R_t, R_{t+1}, \ldots, R_{t+n}$ are determined according to the patient state changing with time by an administered drug and the rewards are discounted by the combined discount rate over time, and wherein evaluation of the target drug dose $a_t$ at the patient state st and algorithm update are performed by $G_{f,t}$ obtained by multiplying each of the rewards $R_t$, $R_{t+1}, \ldots, R_{t+n}$ by the combined discount rate and then adding them all together.

6. The method according to claim 1, wherein the discount rate is a combined discount rate $r^n F_n$ obtained by multiplying a monotonic discount rate $r^n$ and a cumulative pharmacokinetic-pharmacodynamic model $F_n$.

7. A system, comprising:

a processor; and memory for storing one or more programs for execution by the processor, the one or more programs including instructions for:

determining a diabetic patient's pharmacokinetic-pharmacodynamic (PK-PD) model;

training a reinforcement learning algorithm for the diabetic patient using insulin infusion data and patient state data based on the pharmacokinetic-pharmacodynamic model, including:

identifying a plurality of selectable insulin doses including at least two predefined non-zero insulin doses;

obtaining the diabetic patient's treatment record including the insulin infusion data and the patient state data associated with a plurality of infusion events, wherein each infusion event corresponds to a respective one of the plurality of selectable insulin doses, a prior patient state, and a post patient state;

obtaining one or more reward criteria corresponding to a plurality of patient states including an underinfusion state, an overinfusion state, and a normal state;

based on the diabetic patient's treatment record, determining a plurality of transition probabilities for a plurality of state transitions among the plurality of patient states, each transition probability indicating a probability of a respective state change when a respective insulin dose is applied, wherein each respective patient state corresponds to a plurality of groups of transition probabilities for state transitions starting from the respective patient state, and each group of transition probabilities corresponds to a distinct predefined non-zero insulin dose and a total transition probability that is equal to 1;

determining a respective reward score for each of the plurality of state transitions based on the one or more reward criteria;

applying a discount rate to the respective reward score associated with each of the plurality of state transitions based on the diabetic patient's PK-PD model; and determining the reinforcement learning algorithm based on a long-term expected reward;

while infusing insulin to the diabetic patient by an insulin infusion pump, time, automatically determining a continuous insulin infusion rate by the trained reinforcement learning algorithm, including:

determining a current insulin dose and a current patient state;

applying the trained reinforcement learning algorithm to determine one or more subsequent insulin doses based on the current insulin dose and the current patient state, including:

determining a first reward for a first transition to a distinct patient state based on a first reward criterion of the one or more reward criteria of the diabetic patient;

determining a time-dependent discount rate corresponding to the first transition for the first reward; and adjusting the first reward associated with the first transition based on the time-dependent discount rate; and continuously controlling the insulin infusion pump to infuse the insulin to the diabetic patient based on the continuous insulin infusion rate that is determined based on the trained reinforcement learning algorithm, such that a blood glucose level of the diabetic patient is maintained in a normal range to protect the diabetic patient from hypoglycemia.

8. The system of claim 7, wherein the reinforcement learning algorithm corresponds to a plurality of pharmacokinetic-pharmacodynamic characteristics associated with the pharmacokinetic-pharmacodynamic model.

9. The system of claim 7, wherein the trained reinforcement learning algorithm divides drug effects in the pharmacokinetic-pharmacodynamic model into short-term drug effects and cumulative drug effects.

10. The system of claim 9, wherein the short-term drug effects use the pharmacokinetic-pharmacodynamic model as the discount rate, and the cumulative drug effects use an integral value of the pharmacokinetic-pharmacodynamic model as the discount rate.

11. The system of claim 7, wherein the discount rate is a combined discount rate $r^n f_n$ obtained by multiplying a monotonic discount rate $r^n$ and the pharmacokinetic-pharmacodynamic model $f_n$.

12. The system of claim 7, wherein the reinforcement learning algorithm selects $a_t$ as a target drug dose at the patient state St at time t, and rewards $R_t$, $R_{t+1}$, . . . , $R_{t+n}$ are determined according to the patient state changing with time by an administered drug and the rewards are discounted by the combined discount rate over time, and wherein evaluation of the target drug dose $a_t$ at the patient state st and algorithm update are performed by $G_{f,t}$ obtained by multiplying each of the rewards $R_t$, $R_{t+1}$, . . . , $R_{t+n}$ by the combined discount rate and then adding them all together.

13. The system of claim 7, wherein the discount rate is a combined discount rate $r^nF_n$ obtained by multiplying a monotonic discount rate $r^n$ and a cumulative pharmacokinetic-pharmacodynamic model $F_n$.

14. A non-transitory computer readable storage medium, storing one or more programs for execution by one or more processors of an apparatus, the one or more programs including instructions for:

determining a diabetic patient's pharmacokinetic-pharmacodynamic (PK-PD) model;

training a reinforcement learning algorithm for the diabetic patient using insulin infusion data and patient state data based on the pharmacokinetic-pharmacodynamic model, including:

identifying a plurality of selectable insulin doses including at least two predefined non-zero insulin doses;

obtaining the diabetic patient's treatment record including the insulin infusion data and the patient state data associated with a plurality of infusion events, wherein each infusion event corresponds to a respective one of the plurality of selectable insulin doses, a prior patient state, and a post patient state;

obtaining one or more reward criteria corresponding to a plurality of patient states including an underinfusion state, an overinfusion state, and a normal state;

based on the diabetic patient's treatment record, determining a plurality of transition probabilities for a plurality of state transitions among the plurality of patient states, each transition probability indicating a probability of a respective state change when a respective insulin dose is applied, wherein each respective patient state corresponds to a plurality of groups of transition probabilities for state transitions starting from the respective patient state, and each group of transition probabilities corresponds to a distinct predefined non-zero insulin dose and a total transition probability that is equal to 1;

determining a respective reward score for each of the plurality of state transitions based on the one or more reward criteria;

applying a discount rate to the respective reward score associated with each of the plurality of state transitions based on the diabetic patient's PK-PD model; and determining the reinforcement learning algorithm based on a long-term expected reward;

while infusing insulin to the diabetic patient by an insulin infusion pump, automatically determining a continuous insulin infusion rate by the trained reinforcement learning algorithm, including:

determining a current insulin dose and a current patient state;

applying the trained reinforcement learning algorithm to determine one or more subsequent insulin doses based on the current insulin dose and the current patient state, including:

determining a first reward for a first transition to a distinct patient state based on a first reward criterion of the one or more reward criteria of the diabetic patient;

determining a time-dependent discount rate corresponding to the first transition for the first reward; and adjusting the first reward associated with the first transition based on the time-dependent discount rate; and continuously controlling the insulin infusion pump to infuse the insulin to the diabetic patient based on the continuous insulin infusion rate that is determined based on the trained reinforcement learning algorithm, such that a blood glucose level of the diabetic patient is maintained in a normal range to protect the diabetic patient from hypoglycemia.

15. The non-transitory computer readable storage medium of claim 14, wherein the reinforcement learning algorithm corresponds to a plurality of pharmacokinetic-pharmacodynamic characteristics associated with the pharmacokinetic-pharmacodynamic model.

16. The non-transitory computer readable storage medium of claim 14, wherein the trained reinforcement learning algorithm divides drug effects in the pharmacokinetic-pharmacodynamic model into short-term drug effects and cumulative drug effects.

17. The non-transitory computer readable storage medium of claim 16, wherein the short-term drug effects use the pharmacokinetic-pharmacodynamic model as the discount rate, and the cumulative drug effects use an integral value of the pharmacokinetic-pharmacodynamic model as the discount rate.

18. The non-transitory computer readable storage medium of claim 14, wherein the discount rate is a combined discount rate $r^nf_n$ obtained by multiplying a monotonic discount rate $r^n$ and the pharmacokinetic-pharmacodynamic model $f_n$.

19. The non-transitory computer readable storage medium of claim 14, wherein the reinforcement learning algorithm selects $a_t$ as a target drug dose at the patient state $s_t$ at time t, and rewards $R_t$, $R_{t+1}$, . . . , $R_{t+n}$ are determined according to the patient state changing with time by an administered drug and the rewards are discounted by the combined discount rate over time, and wherein evaluation of the target drug dose $a_t$ at the patient state st and algorithm update are performed by $G_{f,t}$ obtained by multiplying each of the rewards $R_t$, $R_{t+1}$, . . . , $R_{t+n}$ by the combined discount rate and then adding them all together.

20. The non-transitory computer readable storage medium of claim 14, wherein the discount rate is a combined discount rate $r^nF_n$ obtained by multiplying a monotonic discount rate $r^n$ and a cumulative pharmacokinetic-pharmacodynamic model $F_n$.

* * * * *